(12) United States Patent
Fan et al.

(10) Patent No.: US 10,874,667 B2
(45) Date of Patent: Dec. 29, 2020

(54) PHARMACEUTICAL SALT OF ANTITUMOR HETEROCYCLIC IMIDAZOLE COMPOUND

(71) Applicant: SHANGHAI HUILUN LIFE SCIENCE & TECHNOLOGY CO., LTD., Shanghai (CN)

(72) Inventors: Xing Fan, Shanghai (CN); Wenhua Li, Shanghai (CN); Jihong Qin, Shanghai (CN)

(73) Assignee: Shanghai Huilin Life Scinece & Technology Co., Ltd., Shanghai (CN)

( * ) Notice: Subject to any disclaimer, the term of this patent is extended or adjusted under 35 U.S.C. 154(b) by 0 days.

(21) Appl. No.: 16/341,255

(22) PCT Filed: Oct. 11, 2017

(86) PCT No.: PCT/CN2017/105646
§ 371 (c)(1),
(2) Date: Apr. 11, 2019

(87) PCT Pub. No.: WO2018/068715
PCT Pub. Date: Apr. 19, 2018

(65) Prior Publication Data
US 2020/0038394 A1 Feb. 6, 2020

(30) Foreign Application Priority Data
Oct. 14, 2016 (CN) .......................... 2016 1 0899468

(51) Int. Cl.
*A61K 31/496* (2006.01)
(52) U.S. Cl.
CPC .................. *A61K 31/496* (2013.01)
(58) Field of Classification Search
CPC .. A61K 31/496; A61K 31/502; C07D 471/04; A61P 35/00
See application file for complete search history.

(56) References Cited

U.S. PATENT DOCUMENTS

2008/0200469 A1* 8/2008 Martin .................. A61K 45/06
514/248

FOREIGN PATENT DOCUMENTS

| CN | 1788000 | A | 6/2006 |
|---|---|---|---|
| CN | 104003940 | A | 8/2014 |
| CN | 106146504 | A | 11/2016 |
| JP | 2018505516 | A | 2/2018 |
| WO | 2002/36576 | A1 | 5/2002 |
| WO | 2004/080976 | A1 | 9/2004 |
| WO | 2016/165655 | A1 | 10/2016 |

OTHER PUBLICATIONS

NCI, "What is Cancer?", publ. Feb. 9, 2015, NIH, pp. 1-16 (Year: 2015).*
Mandal, "How to Prevent Cancer", pub Aug. 29, 2013, New Medical Net, http://www.news-medical.net/health/How-to-Prevent-Cancer.aspx , pp. 1-4 (Year: 2013).*
Bhatia et. al., Nature Biotechnology, 2012, NPG, vol. 30(7), pp. 604-610 (Year: 2012).*
Leaf, Fortune, 2004, Time Inc., pp. 1-26 (Year: 2004).*
Kaiser, Science, AAAS, vol. 337, pp. 282-284 (Year: 2012).*
Wistuba et. al., Nature Reviews Clinical Oncology, 2011, NPG, vol. 8, pp. 135-141 (Year: 2011).*
Li et. al., English translation of CN 104003940A, publ Aug. 27, 2014 (Year: 2014).*
International Search Report for PCT/CN2017/105646 dated Jan. 8, 2018.
Menear, Keith A. et al., 4-[3-(4-Cycopropanecarbonylpiperazine-1-carbonyl)-4-fluorobenzyl]-2H-phthalazin-1-one: A Novel Bioavailable Inhibitor of Poly(ADP-ribose) Polymerase-1, J. Med Chem., 2008, 5I, 6851-6591.

* cited by examiner

*Primary Examiner* — Sarah Pihonak
(74) *Attorney, Agent, or Firm* — Kathleen D. Rigaut; Howson & Howson LLP

(57) ABSTRACT

The present invention relates to the field of pharmaceutical synthesis, and in particular to an antitumor heterocyclic imidazole compound (I), namely: a pharmaceutical salt of 4-(3-(4-(1H-imidazo[4,5-b]pyridine-5-yl)piperazine-1-carbonyl)-4-fluorobenzyl)phthalazine-1(dihydro)-ketone, a preparation method therefor, a pharmaceutical composition thereof and a use thereof in the preparation of antitumor drugs. The pharmaceutical salt of the compound (I) in the present invention may be used in the preparation of a medicament for the treatment or prevention of conditions which can be improved by inhibiting PARP activity.

7 Claims, No Drawings

PHARMACEUTICAL SALT OF ANTITUMOR HETEROCYCLIC IMIDAZOLE COMPOUND

CROSS-REFERENCE TO RELATED APPLICATIONS

This application is a § 371 of International Patent Application No. PCT/CN2017/105646, filed Oct. 11, 2017, which claims priority to Chinese Patent Application No. 201610899468.8, filed Oct. 14, 2016. The entire disclosures of each of the aforesaid applications is incorporated by reference in the present application.

BACKGROUND

Technical Field

The present invention relates to the field of pharmaceutical synthesis, and in particular to a pharmaceutically acceptable salt of an antitumor heterocyclic imidazole compound (I), namely: 4-(3-(4-(1H-imidazo[4,5-b]pyridine-5-yl)piperazine-1-carbonyl)-4-fluorobenzyl) phthalazine-1(dihydro)-one, a preparation method therefor, a pharmaceutical composition thereof and use thereof in the preparation of antitumor drugs.

Related Art

Chemotherapy and ionizing radiation therapy are two common methods for treating cancers. Both therapies induce single-strand and/or double-strand breaks of DNA to produce cytotoxic effects, and the target tumor cells are killed due to chromosome damage. In response to the DNA damage signal, an important consequence is that the cell cycle regulatory site signal is activated to protect cells from mitosis in the event of DNA damage, so as to avoid cell damage. In most cases, tumor cells have a high rate of proliferation while exhibiting cell cycle regulatory site signal deficiency. Therefore, it can be inferred that there is a specific DNA repair mechanism in tumor cells, which can quickly respond to and repair chromosomal damage associated with proliferation regulation, so the tumor cells can escape from the cytotoxic effects of some therapeutic agents and survive persistently.

In clinical applications, the effective concentration of a chemotherapeutic agent or the therapeutic radiation intensity can combat these DNA repair mechanisms and ensure the killing effect on target tumor cells. However, tumor cells may be tolerant to treatment by enhancing their mechanisms for DNA damage repair, allowing them to survive deadly DNA damage. In order to overcome the resistance generated, it is usually necessary to increase the dose of the therapeutic agent or increase the radiation intensity. This will adversely affect the normal tissue around the lesion, thereby causing serious adverse reactions during the treatment process, and increasing the risk of treatment. Moreover, the increasing resistance will reduce the therapeutic effect, so it can be inferred that by modulating the repair mechanism of DNA damage signal, the cytotoxicity of a DNA damaging agent can be improved in a tumor cell-specific manner.

Poly(ADP-ribose) polymerases (PARPs) characterized by poly-ADP-ribosylation activity constitute a superfamily of 18 nuclear enzymes and cytoplasmic enzymes. This poly-ADP-ribosylation regulates the catalytic activity and inter-protein interaction of the proteins of interest and regulates many essential biological processes, including DNA repair, cell death, and genomic stability.

PARP-1 activity accounts for approximately 80% of the total cellular PARP activity, and PARP-1, together with its closest counterpart, PARP-2, becomes a member of the PARP family having the ability to repair DNA damage. As a sensor and signaling protein for DNA damage, PARP-1 can rapidly detect and directly bind to sites of DNA damage, and then induce and gather a variety of proteins required for DNA repair, thereby repairing DNA damage. When PARP-1 is deficient in cells, PARP-2 can replace PARP-1 to repair DNA damage. Studies have shown that the expression of PARPs in solid tumors is generally enhanced compared to normal cells.

In addition, tumors with DNA repair-related gene deletions (such as BRCA-1 or BRCA-2), such as breast tumors and ovarian cancer, show extreme sensitivity to PARP-1 inhibitors, suggesting that PARP inhibitors can be potentially used as a single agent in the treatment of this triple negative breast cancer. Furthermore, because the mechanism for DNA damage repair is the main mechanism for tumor cells to produce resistance in response to the chemotherapeutic agent and ionizing radiation therapy, PARP-1 is considered to be an effective target for exploring new cancer treatment methods.

Early developed and designed PARP inhibitors were analogs developed using NAD, a niacinamide that is a PARP catalyzed substrate, as a template. These inhibitors act as competitive inhibitors of NAD and compete with NAD for the catalytic site of PARP, thereby preventing the synthesis of poly(ADP-ribose) chains. PARP without the poly(ADP-ribosylation) modification cannot be dissociated from the DNA damage site, which will cause other proteins involved in the repair to enter the damage site, and the repair process cannot be performed. Thus, under the action of cytotoxic drugs or radiation, the presence of PARP inhibitors ultimately results in the death of tumor cells with damaged DNA.

In addition, NAD, which is consumed as a PARP-catalyzed substrate, is essential for the process of cell synthesis of ATP. At a high level of PARP activity, the intracellular NAD level is significantly reduced, which in turn affects the intracellular ATP level. Due to the insufficient intracellular ATP content, cells cannot achieve the ATP-dependent programmed death and can only turn to the special apoptotic process of necrosis. During the process of necrosis, a large number of inflammatory factors are released, causing toxic effects on other organs and tissues. Therefore, PARP inhibitors can also be used to treat a variety of diseases associated with this mechanism, including neurodegenerative diseases (senile dementia, Huntington's disease, Parkinson's disease), diabetes, ischemia, or complications during ischemia-reperfusion such as myocardial infarction and acute renal failure, circulatory diseases such as septic shock, and inflammatory diseases such as chronic rheumatism.

SUMMARY

The present invention relates to a pharmaceutically acceptable salt of a PARP inhibitor, that is, 4-(3-(4-(1H-imidazo[4,5-b]pyridine-5-yl)piperazine-1-carbonyl)-4-fluorobenzyl) phthalazine-1(dihydro)-one. The PARP inhibitor 4-(3-(4-(1H-imidazo[4,5-b]pyridine-5-yl) piperazine-1-carbonyl)-4-fluorobenzyl)phthalazine-1(dihydro)-one has a structure below (Formula I):

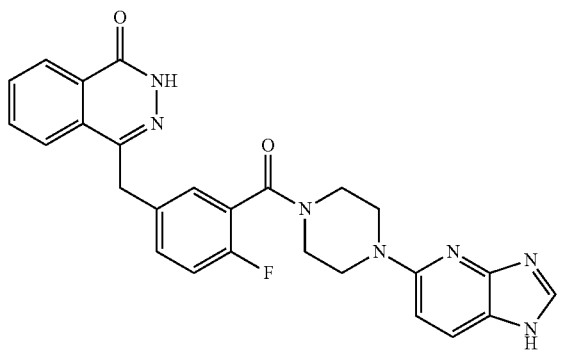

(I)

The structural formula of Formula (I) in the present invention has a certain basicity and a pharmaceutically acceptable salt can be formed by reaction with a corresponding organic acid or inorganic acid. Accordingly, the present invention provides a pharmaceutically acceptable salt of the compound of Formula (I) with an organic or inorganic acid.

Salts of the compound of Formula (I) with an organic acid include, but are not limited to, salts formed with formic acid, acetic acid, trifluoroacetic acid, methanesulfonic acid, ethanesulfonic acid, benzenesulfonic acid, p-toluenesulfonic acid, benzoic acid, citric acid, fumaric acid, malic acid, maleic acid, tartaric acid, lactic acid, isethionic acid or the like. Salts of the compound of Formula (I) with an inorganic acid include, but are not limited to, salts formed with hydrochloric acid, hydrobromic acid, phosphoric acid, sulfuric acid, oxalic acid, nitric acid, and the like.

Preferably, the pharmaceutically acceptable salt of the compound of Formula (I) of the present invention is a hydrochloride, a hydrobromide, a methanesulfonate, a p-toluenesulfonate, a benzenesulfonate or a hydroxyethanesulfonate. Hydrochloride, sulfate, phosphate, methanesulfonate, p-toluenesulfonate, benzenesulfonate, and hydroxyethanesulfonate are further preferred. Hydrochloride, methanesulfonate, p-toluenesulfonate, benzenesulfonate, and hydroxyethanesulfonate are most preferred.

The pharmaceutically acceptable salt of the compound of Formula (I) of the present invention, particularly the hydrochloride, methanesulfonate, p-toluenesulfonate, benzenesulfonate, or hydroxyethanesulfonate, has superior physical and chemical properties, and remarkably improved solubility and dissolution rate, compared to the compound of Formula (I) before salt formation, where the solubility is increased by at least 10 times relative to the compound of Formula (I). Therefore, the pharmaceutically acceptable salt is more suitable for the production of various pharmaceutical dosage forms and improves the in-vivo bioavailability as compared with the compound of Formula (I) in free base form.

In another aspect, the present invention provides a method for preparing a pharmaceutically acceptable salt of 4-(3-(4-(1H-imidazo[4,5-b]pyridine-5-yl)piperazine-1-carbonyl)-4-fluorobenzyl)phthalazine-1(dihydro)-one of Formula (I).

In general, salts of a basic compound can be prepared by ion exchange chromatography, or by reacting the free base with a stoichiometric amount or excess of a desired salt-forming inorganic or organic acid in a suitable solvent or combination of solvents.

Accordingly, the pharmaceutically acceptable salt of the compound of Formula (I) of the present invention can be obtained through acid-base reaction of the compound (I) with a corresponding acid, for example, a corresponding inorganic acid, organic acid or polymeric acid.

In the above method for preparing a pharmaceutically acceptable salt of the compound (I) of the present invention through acid-base reaction, an organic solvent, preferably a polar solvent such as an alcohol solvent, acetonitrile or acetone, may be used as a reaction solvent; or a mixed solvent of an organic solvent and water may be used.

In one embodiment, the pharmaceutically acceptable salt of the present invention contains 1 equivalent of the compound of Formula (I) and 1 equivalent of an acid. In one embodiment, the method for preparing a pharmaceutically acceptable salt of the compound of Formula (I) according to the invention comprises reacting 4-(3-(4-(1H-imidazo[4,5-b]pyridine-5-yl)piperazine-1-carbonyl)-4-fluorobenzyl)phthalazine-1(dihydro)-one with a corresponding inorganic or organic acid in an organic solvent.

For example, in a preferred embodiment, the method for preparing a pharmaceutically acceptable salt of the present invention comprises reacting 4-(3-(4-(1H-imidazo[4,5-b]pyridine-5-yl)piperazine-1-carbonyl)-4-fluorobenzyl)phthalazine-1(dihydro)-one with hydrochloric acid in a single or mixed solvent of a $C_1$-$C_4$ alcohol or a $C_3$-$C_5$ ketone.

For example, in a preferred embodiment, the method for preparing a pharmaceutically acceptable salt of the present invention comprises reacting 4-(3-(4-(1H-imidazo[4,5-b]pyridine-5-yl)piperazine-1-carbonyl)-4-fluorobenzyl)phthalazine-1(dihydro)-one with methanesulfonic acid in a single or mixed solvent of a $C_1$-$C_4$ alcohol or a $C_3$-$C_5$ ketone.

For example, in a preferred embodiment, the method for preparing a hydrochloride of the compound of Formula (I) of the present invention comprises reacting 4-(3-(4-(1H-imidazo[4,5-b]pyridine-5-yl)piperazine-1-carbonyl)-4-fluorobenzyl)phthalazine-1(dihydro)-one with hydrochloric acid in a single or mixed solvent of a $C_1$-$C_4$ alcohol or a $C_3$-$C_5$ ketone, where the $C_1$-$C_4$ alcohol is optionally selected from methanol, ethanol, n-propyl alcohol, or n-butyl alcohol; and the $C_3$-$C_5$ ketone is optionally selected from acetone, butanone, or pentanone. The reaction temperature is 10 to 60° C., preferably 10 to 50° C., and more preferably 20 to 40° C.

In a further aspect, the present invention provides a pharmaceutical composition comprising a pharmaceutically acceptable salt of the compound of Formula (I), in particular, a hydrochloride, a methanesulfonate, a p-toluenesulfonate, a benzenesulfonate, or a hydroxyethanesulfonate of the compound of Formula (I), in combination with one or more of pharmaceutically acceptable carriers or excipients.

In still another aspect, the present invention provides the use of a pharmaceutically acceptable salt of the compound of Formula (I) in the preparation of a medicament for inhibiting the activity of poly(ADP-ribose) polymerase (PARP). The present invention also provides a method for the treating or preventing a condition that can be ameliorated by inhibiting poly(ADP-ribose) polymerase (PARP), comprising administering to a patient in need thereof an effective amount of a pharmaceutically acceptable salt of Compound I or a composition comprising the salt.

Further, the condition that can be ameliorated by inhibiting poly(ADP-ribose) polymerase (PARP) includes cancers, for example, gastric cancer, pancreatic cancer, leukemia, breast cancer, ovarian cancer, prostate cancer and so on.

The compound of the invention can also be used to treat homologous recombination (HR)-dependent DNA double-strand break (DSB) repair activity deficient cancers.

The HR-dependent DNA double-strand break (DSB) repair activity deficient cancer may comprise or consist of one or more cancer cells having reduced or lost ability to repair DNA DSBs by this pathway compared to normal cells. That is, in one or more cancer cells, the activity of the HR-dependent DNA DSB repair pathway may be reduced or lost.

In one or more cancer cells of an individual having a HR-dependent DNA DSB repair activity deficient cancer, the activity of one or more components of the HR dependent DNA DSB repair pathway may be lost. The components of the HR dependent DNA DSB repair pathway have been well characterized in the art.

The compound of the present invention can be administered to a subject alone or in a pharmaceutical composition in combination with a pharmaceutically acceptable carrier, excipient, diluent, auxiliary, filler, buffer, stabilizer, preservative, and lubricant, according to standard pharmaceutical practice.

The compound of the invention can be administered to a subject by any convenient route of administration, whether systemic/peripheral or at the desired site of action, including but not limited to oral administration; topical administration; pulmonary administration; rectal administration; vaginal administration; parenteral administration; and administration via an implanted depot.

When the compound of the invention is administered to a subject, the selected dosage level will depend on a variety of factors including, but not limited to, activity of a particular compound, severity of the individual's symptoms, route of administration, time of administration, excretion rate of the compound, duration of treatment, combined use of other drugs, compounds and/or materials, as well as the patient's age, gender, weight, status, general health status and previous treatment history. The amount of the compound and the route of administration are ultimately determined by the physician, although generally the dosage will achieve a local concentration at the site of action that achieves the desired effect without causing substantially harmful or toxic side effects.

In vivo administration can be achieved in a single dose, continuously or intermittently throughout the course of treatment. Methods for determining the most effective mode of administration and dosage are well known to those skilled in the art and will vary with the preparation used for treatment, the purpose of treatment, the target cell being treated and the subject being treated. Single or multiple administrations can be made using dosage levels and regimes determined by the physician.

The compound of the invention may also be used in combination with an anticancer or chemotherapeutic agent.

The compound of the invention is useful as a chemosensitizer and radiosensitizer for the treatment of cancers. It can be used to treat patients who have previously experienced or are currently undergoing cancer treatment. Such previous treatments include pre-chemotherapy, radiotherapy, surgery or immunotherapy, such as cancer vaccines. Accordingly, the present invention provides a combination of a pharmaceutically acceptable salt of Compound I and an anticancer agent for simultaneous, separate or sequential administration.

The present invention also provides a combination of a pharmaceutically acceptable salt of Compound I with radiotherapy, and an anticancer agent for simultaneous, separate or sequential administration.

The present invention also provides use of a pharmaceutically acceptable salt of Compound I in the preparation of a medicament for use as an adjunct to cancer therapy or for enhancing the killing effect on tumor cells by use in combination with ionizing radiation or a chemotherapeutic agent.

The present invention also provides use of a pharmaceutically acceptable salt of Compound I in the preparation of a medicament for use as an adjunct to cancer therapy or for enhancing the killing effect on tumor cells by use in combination with ionizing radiation or a chemotherapeutic agent. The compound can also be used in combination with ionizing radiation or chemotherapeutic agents.

These and other aspects of the invention will be apparent from the teachings herein.

In still another aspect of the present invention, a method for preparing the compound of Formula (I) is provided, which comprises reacting a compound 6 and a compound 4 in the presence of a condensing agent. In a specific embodiment, the condensing agent is 2-(7-azobenzotriazole)-N,N,N',N'-tetramethyluronium hexafluorophosphate, and the synthetic route is as follows:

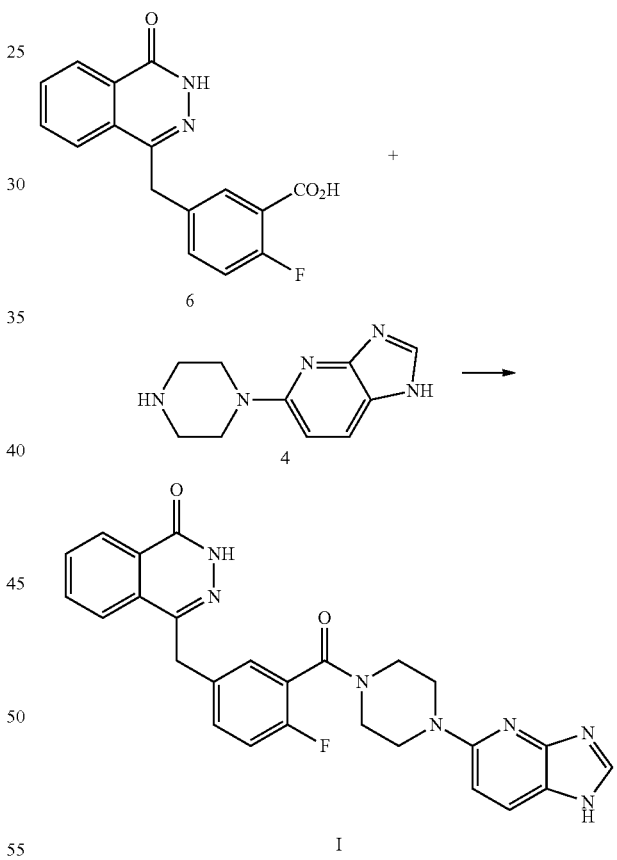

It has been found that 5-(piperazine-1-yl)-1H-imidazo[4,5-b]pyridine (Compound 4) can be prepared by the following procedure: 4-(6-amino-5-nitropyridine-2-yl) piperazine-1-tert-butyl carbonate (Compound 1) is hydrogenated to prepare 4-(5,6-diaminopyridine-2-yl)piperazine-1-tert-butyl carbonate (Compound 2), which is then reacted with trimethyl orthoformate to prepare 4-(1H-imidazo[4,5-b]pyridine-5-yl)piperazine-1-tert-butyl carbonate (Compound 3), which is deprotected to give Compound 4. The specific synthetic route is as follows:

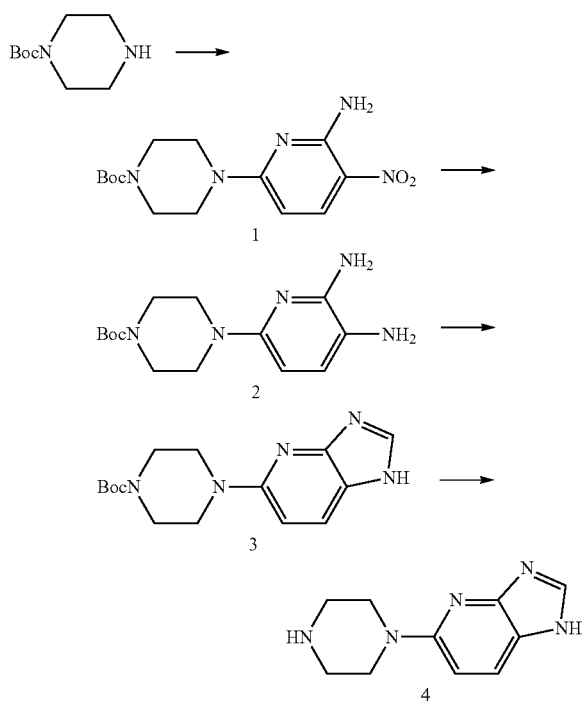

DETAILED DESCRIPTION

Example 1: Preparation of Compound 4 Following Route I

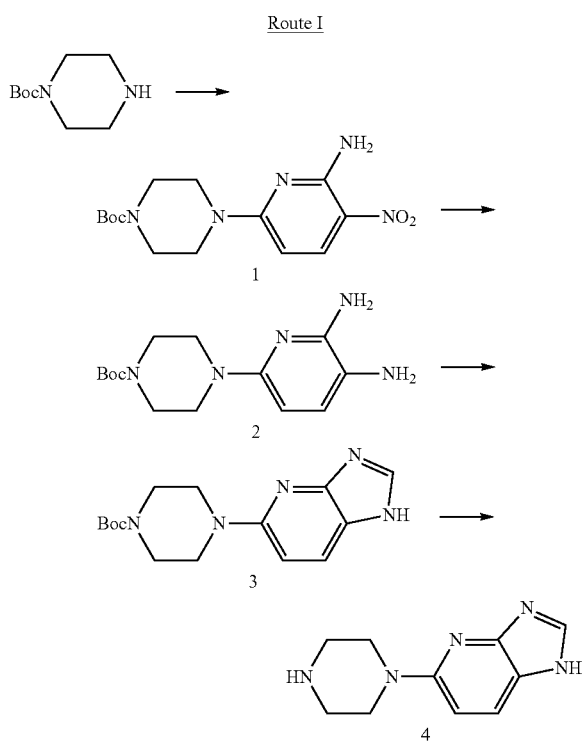

Step 1: Preparation of t-butyl 4-(6-amino-5-nitropyridine-2-yl)piperazine-1-carbonate (Compound 1)

To the compound mono-t-butoxycarbonyl protected piperazine (1.86 g, 10 mmol) dissolved in dimethyl formamide (10 mL), 6-chloro-3-nitro-2-aminopyridine (1.91 g, 11 mmol) and diisopropylethyl amine (1.55 g, 12 mmol) were added, and reacted at room temperature for 8 hrs. Then the solvent was removed under reduced pressure, and the residue was separated by flash column chromatography (dichloromethane:methanol=50:1), to obtain white solid Compound 1: t-butyl 4-(6-amino-5-nitropiperidine-2-yl)piperazine-1-carbonate (2.72 g, yield 84%). MS(ESI) m/z: $[M+H]^+$=324.

Step 2: Preparation of t-butyl 4-(5,6-diaminopyridine-2-yl)piperazine-1-carbonate (Compound 2): 10% palladium on carbon (259 mg) was added to a solution of Compound 1 (2.59 g, 8 mmol) dissolved in methanol (20 mL), hydrogenated for 7 hrs at normal temperature, and filtered. The residue was separated by flash column chromatography (dichloromethane:methanol=10:1), to obtain yellow solid Compound 2: t-butyl 4-(5,6-diaminopiperidine-2-yl)piperazine-1-carbonate (2.25 g, yield 93%). MS(ESI) m/z: $[M+H]^+$=294.

Step 3: Preparation of t-butyl 4-(1H-imidazo[4,5-b]pyridine-5-yl)piperazine-1-carbonate (Compound 3): To a solution of Compound 2 (1.47 g, 5 mmol) dissolved in trimethyl orthoformate (6 g), p-toluenesulfonic acid (86 mg, 0.5 mmol) was added, heated to reflux, reacted for 8 hrs and then cooled. The solvent was removed under reduced pressure, and the residue was separated by flash column chromatography (dichloromethane:methanol=10:1), to obtain light yellow solid Compound 3: t-butyl 4-(1H-imidazo[4,5-b]pyridine-5-yl)piperazine-1-carbonate (0.73 g, yield 48%). MS(ESI) m/z: $[M+H]^+$=304.

Step 4: Preparation of 5-(piperazine-1-yl)-1H-imidazo[4,5-b]pyridine (Compound 4): To a solution of Compound 3 (1.52 g, 5 mmol) dissolved in dichloromethane (10 mL), trifluoroacetic acid (2.28 g, 20 mmol) was added, and reacted at room temperature for 8 hrs. The solvent was removed under reduced pressure, and the residue was taken up in dichloromethane (20 mL), adjusted to pH 8 with sodium bicarbonate, and concentrated to remove the solvent. The residue was separated by flash column chromatography (dichloromethane:methanol=10:1), to obtain light yellow solid Compound 4: 5-(piperazine-1-yl)-1H-imidazo[4,5-b]pyridine (0.87 g, yield 86%, purity 95.0% by HPLC). MS(ESI) m/z: $[M+H]^+$=204.

Example 2: Preparation of Compound 6 Following Route II

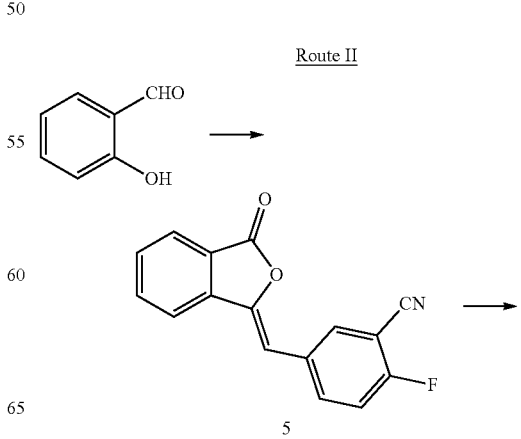

-continued

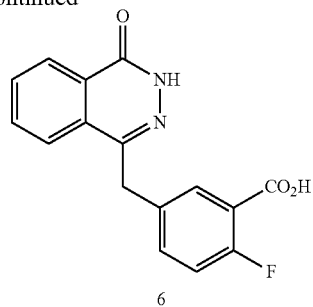

6

Step 1: Preparation of 2-fluoro-4-((3-oxoisobenzofuran-1 (3H)-ylidene)methyl) benzonitrile (Compound 5): In an ice bath, to a solution of sodium methoxide (61.8 g, 1.14 mol) dissolved in anhydrous methanol (1 L), dimethyl phosphite (97 mL, 1.06 mol) was slowly added. The temperature of the reaction system was maintained below 5° C., and 2-carboxybenzaldehyde (135 g, 0.9 mol) was slowly added dropwise over 20 min. The reaction system was gradually heated to room temperature, and methylsolfuonic acid (81.6 mL, 1.26 mol) was added dropwise in half an hour. The solvent was removed under reduced pressure, and the residue was diluted with water (600 mL), and extracted three times with dichloromethane (500 mL). The organic layers were combined, and extracted twice with water (100 mL). Then, the organic phase was dried over anhydrous magnesium sulfate. The solvent was removed under reduced pressure, to obtain a light yellow solid compound: dimethyl (3-oxo-1,3-dihydroisobenzofuran-1-yl)phosphite, which was directly used in the next reaction without purification. To a solution of the compound dimethyl (3-oxo-1,3-dihydroisobenzofuran-1-yl) phosphite (35 g, 0.14 mol) obtained without purification in the previous reaction dissolved in tetrahydrofuran (330 mL), 2-fluoro-5-formylbenzonitrile (20.9 g, 0.14 mol) was added. The system was cooled to 15° C., and triethyl amine (19.5 mL, 0.14 mol) was slowly added dropwise over 30 min. The reaction system was gradually heated to room temperature. The solvent was removed under reduced pressure, and the residue was slurried in water (250 mL), and filtered, to obtain white solid Compound 5: 2-fluoro-4-((3-oxoisobenzofuran-1(3H)-ylidene)methyl) benzonitrile (37.2 g, yield 96%).

Step 2: Preparation of 2-fluoro-5-((4-oxo-3,4-dihydrophthalazine-1-yl)methyl)benzoic acid (Compound 6): To a solution of Compound 5 (37 g, 0.14 mol) in water (200 mL), a 13N sodium hydroxide solution (50 mL) was added, heated to 90° C., and stirred for 1 hr. The reaction system was cooled to 70° C., and then hydrazine hydrate (100 mL, 2 mol) was added, and stirred for 18 hrs while being maintained at this temperature. The reaction solution was cooled to room temperature, adjusted to pH 4 with 8N hydrochloric acid, and filtered. The filter cake was sequentially washed twice with water (60 mL) and three times with diethyl ether (50 mL), and dried under vacuum to obtain white solid Compound 6: 2-fluoro-5-((4-oxo-3,4-dihydrophthalazine-1-yl)methyl)benzoic acid (30.1 g, yield 77%). MS(ESI) m/z: [M+H]$^+$=299.

Example 3

Preparation of Compound of Formula (I)

To a solution of Compound 4 (50 mg, 0.17 mmol) dissolved in dimethyl formamide (5 mL), Compound 6 (49 mg, 0.24 mmol), 2-(7-azobenzotriazole)-N,N,N',N'-tetramethyluronium hexafluorophosphate (77 mg, 0.2 mmol), and triethyl amine (70 mg, 0.7 mmol) were added, and stirred at room temperature overnight. The solvent was removed by concentration, and the residue was separated by flash column chromatography (dichloromethane:methanol=10:1), to obtain white solid Compound (I): 4-(3-(4-(1H-imidazo[4,5-b]pyridine-5-yl)piperazine-1-carbonyl)-4-fluorobenzyl)phthalazine-1(dihydro)-one (16 mg, yield 20%). MS (ESI) m/z: [M+H]$^+$=484. $^1$H NMR (300 MHz, DMSO-d6): δ 12.61 (br, 1H), 8.27-8.24 (m, 1H), 8.16 (s, 1H), 8.00-7.97 (m, 1H), 7.93-7.82 (m, 4H), 7.45-7.39 (m, 2H), 7.28-7.22 (m, 1H), 6.83-6.80 (m, 1H), 4.34 (s, 2H), 3.73 (br, 2H), 3.58 (br, 2H), 3.42 (br, 4H).

Example 4

Preparation of 4-(3-(4-(1H-imidazo[4,5-b]pyridine-5-yl)piperazine-1-carbonyl)-4-fluorobenzyl)phthalazine-1(dihydro)-one Hydrochloride To a solution of the compound of Formula (I) (3 g, 6.21 mmol) dissolved in ethanol (30 ml), hydrochloride acid (2.1 ml, 24.84 mmol) was added dropwise, and reacted at 25° C. with stirring for 5 hrs. The reaction solution was filtered, and dried to obtain an off white solid that is a hydrochloride of the compound of Formula (I): 4-(3-(4-(1H-imidazo[4,5-b]pyridine-5-yl)piperazine-1-carbonyl)-4-fluorobenzyl)phthalazine-1(dihydro)-one hydrochloride (3.0 g, yield 93%). Elemental analysis: Theoretical Cl: 6.47%; Found Cl: 6.58%. The salt forming ratio of the compound of Formula (I) to HCl is determined to be 1:1.

MS (ESI) m/z: [M+H]$^+$=484. $^1$H NMR (300 MHz, DMSO-d6): δ 12.62 (s, 1H), 9.42 (s, 1H), 8.24-8.22 (m, 1H), 8.02 (d, 1H), 7.94 (d, 1H), 7.88-7.79 (m, 2H), 7.46-7.39 (m, 2H), 7.23 (t, 1H), 7.9 (d, 1H), 4.32 (s, 2H), 3.75 (br, 2H), 3.69 (br, 2H), 3.53 (br, 2H), 3.32 (br, 2H).

Example 5

Preparation of 4-(3-(4-(1H-imidazo[4,5-b]pyridine-5-yl)piperazine-1-carbonyl)-4-fluorobenzyl)phthalazine-1(dihydro)-one Methanesulfonate To a solution of the compound of Formula (I) (3 g, 6.21 mmol) in acetone (30 ml), methanesulfonic acid (2.38 g, 24.84 mmol) was added, and stirred at 30° C. for 10 h. The reaction solution was filtered, and dried to obtain an off white solid, that is a methanesulfonate of the compound of Formula (I): 4-(3-(4-(1H-imidazo[4,5-b]pyridine-5-yl)piperazine-1-carbonyl)-4-fluorobenzyl)phthalazine-1(dihydro)-onemethanesulfonate (3.16 g, yield 88%). Elemental analysis: Theoretical S: 5.36%; Found S: 5.34%. The salt forming ratio of the compound of Formula (I) to methanesulfonic acid is determined to be 1:1.

MS (ESI) m/z: [M+H]$^+$=484. $^1$H NMR (300 MHz, DMSO-d6): δ 12.60 (s, 1H), 9.41 (s, 1H), 8.24-8.22 (m, 1H), 8.02 (d, 1H), 7.94 (d, 1H), 7.89-7.79 (m, 2H), 7.47-7.39 (m, 2H), 7.23 (t, 1H), 7.9 (d, 1H), 4.32 (s, 2H), 3.75 (br, 2H), 3.69 (br, 2H), 3.53 (br, 2H), 3.32 (br, 2H), 2.46 (s, 3H).

Example 6

Preparation of 4-(3-(4-(1H-imidazo[4,5-b]pyridine-5-yl)piperazine-1-carbonyl)-4-fluorobenzyl)phthalazine-1(dihydro)-one p-toluenesulfonate To a solution of the compound of Formula (I) (1 g, 2.07 mmol) dissolved in acetone (10 ml), p-toluenesulfonic acid (1.07 g, 6.21 mmol) was added, and stirred at 20° C. for 10 hrs. The reaction solution was filtered, and dried to obtain an off white solid that is a p-toluenesulfonate of the compound of Formula (I): 4-(3-(4-(1H-imidazo[4,5-b]pyridine-5-yl)piperazine-1-carbonyl)-4-fluorobenzyl)phthalazine-1(dihydro)-one p-toluenesulfonate (1.22 g, yield 90%). Elemental analysis: Theoretical S: 4.88%; Found S: 4.90%. The salt forming ratio of the compound of Formula (I) to p-toluenesulfonic acid is 1:1. MS (ESI) m/z: [M+H]$^+$=484.

Example 7

Preparation of 4-(3-(4-(1H-imidazo[4,5-b]pyridine-5-yl)piperazine-1-carbonyl)-4-fluorobenzyl)phthalazine-1(dihydro)-one Benzenesulfonate To a solution of the compound of Formula (I) (1 g, 2.07 mmol) dissolved in acetone (10 ml), benzenesulfonic acid (1.31 g, 8.28 mmol) was added, and stirred at 35° C. for 20 hrs. The reaction solution was filtered, and dried to obtain an off white solid, that is a benzenesulfonate of the compound of Formula (I): 4-(3-(4-(1H-imidazo[4,5-b]pyridine-5-yl)piperazine-1-carbonyl)-4-fluorobenzyl)phthalazine-1(dihydro)-one benzenesulfonate (1.13 g, yield 85%). Elemental analysis: Theoretical S: 4.99%; Found S: 5.05%. The salt forming ratio of the compound of Formula (I) to benzenesulfonic acid is 1:1. MS (ESI) m/z: [M+H]$^+$=484.

Example 8

Preparation of 4-(3-(4-(1H-imidazo[4,5-b]pyridine-5-yl)piperazine-1-carbonyl)-4-fluorobenzyl)phthalazine-1(dihydro)-one Hydroxyethanesulfonate To a solution of the compound of Formula (I) (1 g, 2.07 mmol) dissolved in acetone (10 ml), hydroxyethanesulfonic acid (1.04 g, 8.28 mmol) was added, and stirred at 25° C. for 20 hrs. The reaction solution was filtered, and dried to obtain an off white solid, that is a hydroxyethanesulfonate of the compound of Formula (I): 4-(3-(4-(1H-imidazo[4,5-b]pyridine-5-yl)piperazine-1-carbonyl)-4-fluorobenzyl)phthalazine-1(dihydro)-one hydroxyethanesulfonate (1.03 g, yield 82%). Elemental analysis: Theoretical S: 5.25%; Found S: 5.10%. The salt forming ratio of the compound of Formula (I) to hydroxyethanesulfonic acid is 1:1. MS (ESI) m/z: [M+H]$^+$=484.

Example 9

Solubility Test

The solubility of the salt of the compound of Formula (I) of the present invention was determined by the following method:

a) About 200 mg of the salt of the compound of Formula (I) was accurately weighed, dissolved in 200 ml of an aqueous solution, stirred at a constant temperature for 30 min, and allowed to stand. The supernatant was centrifuged, and then the supernatant of the centrifugate was taken and used as a test solution.

b) About 200 mg of the compound of Formula (I) was accurately weighed, dissolved in aqueous methanol, and quantitatively diluted into a solution containing 0.02 mg of free base per 1 ml.

The solution was used as a reference solution.

C) The blank solvent, the reference solution and the test solution were each 10 M, and the peak area was measured by high performance liquid chromatography and recorded, and the solubility of the salt in water was calculated.

The table below compares the solubilities of the compound of Formula (I) and its various forms of salts. Table 1 shows an unexpected improvement in the water solubility of the compound of Formula (I) after salt formation.

TABLE 1

Comparison of solubilities

| Test compound | Solubility in water |
| --- | --- |
| Formula I | 1 μg/ml |
| Hydrochloride of the compound of Formula I | 340 μg/ml |
| Methanesulfonate of the compound of Formula I | 300 μg/ml |
| p-toluenesulfonate of the compound of Formula I | 40 μg/ml |
| Benzenesulfonate of the compound of Formula I | 230 μg/ml |
| Hydroxyethanesulfonate of the compound of Formula I | 310 μg/ml |

Example 10

Biological Evaluation

Poly ADP ribosylation of nuclear proteins is post-translational in response to DNA damage. PARP is the abbreviation of poly(ADP-ribose) polymerase, which catalyzes the binding of poly(ADP-ribose) to adjacent nuclear proteins in the presence of NAD, thereby triggering a DNA repair mechanism via the base-excision repair pathway. The level of binding of this biotinylated ADP-ribose to histones can be determined by using Trevigen's HT Universal Chemiluminescent PARP Assay Kit.

Reagents and Materials:

1. HT Universal Chemiluminescent PARP Assay Kit with Hi stone-coated Strip Wells, Trevigen, Product catalog: 4676-096-K 2. Plate reader, Perkin Elmer, EnVision Multilabel Plate Reader Solutions and Buffers 1. Washing buffer containing 0.1% Triton X-100 in PBS 2. 20×PARP buffer, which was 20-fold diluted with deionized water to give 1× buffer, which was used to dilute the recombinant PARP enzyme, PARP Cocktail and the tested compound.

3. 10×PARP Cocktail prepared with 10×PARP Cocktail following the method below: 10×PARP Cocktail 2.5 μl/well, 10× activated DNA 2.5 al/well, 1×PARP buffer 20 μl/well.

4. PARP Enzyme, which was carefully diluted with 1×PARP buffer only before use, where the diluted enzyme solution should be used as soon as possible, and if it is not used up, it should be discarded.

5. Strep-HRP, which was only 500-fold diluted with 1× Strep diluent to obtain 1× solution before use.

6. Chemiluminescent substrates, in which the same volume of PeroxyGlow A and B solutions were only mixed uniformly before use to obtain a substrate for horseradish peroxidase.

Experimental Method:

Formulation of Compound

1. The mother liquor of the test compound of Formula (I) of 10 mM was diluted to 10 μM, and 1 μM with DMSO.

2. Immediately before use, solutions over gradient concentrations of the compound of Formula (I) dissolved in DMSO were 20-fold diluted with 1×PARP buffer, to obtain a 5× compound solution which was used for detection. The positive control (POSITIVE) and negative control (NEGATIVE) wells were 1×PARP buffer (with 5% DMSO).

Operation Steps

1. The histone was moistened with 50 M 1×PPAR buffer per well, and the plate was incubated for 30 minutes at room temperature. Then the 1×PARP buffer in the wells was aspirated and the residual liquid was tapped off on a paper towel.

2. According to the arrangement pattern of the compound, the diluted 5× compound solution was added to the corresponding wells in 10 μl per well, and the positive control (POSITIVE) and negative control (NEGATIVE) wells were 1×PARP buffer (with 5% DMSO)

3. The PARP enzyme was diluted to 0.5 Unit per 15 M solution with PARP buffer, then 15 M enzyme solution was added to the wells except for the negative control well, the negative control well was only added with 1×PARP buffer, and the plate was incubated for 10 minutes at room temperature.

4. 250 μl of 1×PARP Cocktail was further added to each well.

5. The plate was incubated for 60 minutes at 27° C.

6. After the incubation, the reaction solution in the well was aspirated and the residual liquid was tapped off on a paper towel. The plate was then washed 4 times with 200 μl per well of a PBS solution containing 0.1% Triton X-100, and the residual liquid was tapped off on a paper towel.

7. Next, the diluted 1× Strep-HRP solution was added to each well, and then the plate was incubated at 27° C. for 60 minutes.

8. After the incubation, the reaction solution in the well was aspirated and the residual liquid was tapped off on a paper towel. The plate was then washed 4 times with 200 μl per well of a PBS solution containing 0.1% Triton X-100, and the residual liquid was tapped off on a paper towel.

9. After the plate was washed, the same volume of PeroxyGlow A and B solutions were mixed well and 100 μl was added to each well. Then, the plate was immediately placed on a plate reader to record the chemiluminescence signal.

Data Processing

The readings in each well were converted to inhibition rates. The inhibition rate of the compound can be calculated using the following formula:

$$\text{Inhibition rate (\%)} = \frac{\text{Reading of the positive control well} - X}{\text{Reading of the positive control well} - \text{Reading of the negative control well}} \times 100\%$$

Note: The reading of the positive control well is the reading of positive well, meaning 100% activity of the enzyme. The reading of the negative control well is the reading of negative well, meaning 0% activity of the enzyme. Activity X is the reading for each concentration of each sample.

The inhibitory activity $IC_{50}$ of the compound of Formula (I) against PARP-1 enzyme is 1 nM and thus the compound has extremely strong inhibitory activity.

What is claimed is:

1. A pharmaceutically acceptable salt of 4-(3-(4-(1H-imidazo[4,5-b]pyridine-5-yl)piperazine-1-carbonyl)-4-fluorobenzyl)phthalazine-1(dihydro)-one, said salt being formed by reaction with an organic acid or inorganic acid selected from a formate, an acetate, a trifluoroacetate, a methanesulfonate, an ethanesulfonate, a benzenesulfonate, a p-toluenesulfonate, a benzoate, a citrate, a fumarate, a malate, a maleate, a tartrate, a lactate, an hydroxyethanesulfonate, a hydrochloride, a hydrobromide, a phosphate, a sulfate, an oxalate and a nitrate.

2. The pharmaceutically acceptable salt according to claim 1, which is formed by reaction with a hydrochloride, a methanesulfonate, a p-toluenesulfonate, a benzenesulfonate, or an hydroxyethanesulfonate.

3. The pharmaceutically acceptable salt according to claim 1, which is 4-(3-(4-(1H-imidazo[4,5-b]pyridine-5-yl) piperazine-1-carbonyl)-4-fluorobenzyl)phthalazine-1(dihydro)-one hydrochloride or 4-(3-(4-(1H-imidazo[4,5-b] pyridine-5-yl)piperazine-1-carbonyl)-4-fluorobenzyl) phthalazine-1(dihydro)-one methanesulfonate.

4. A pharmaceutical composition, comprising a pharmaceutically acceptable salt according to claim 1, and a pharmaceutically acceptable carrier.

5. A method for inhibiting PARP activity in a subject in need thereof, comprising administrating an effective amount of a pharmaceutically acceptable salt of 4-(3-(4-(1H-imidazo[4,5-b]pyridine-5-yl)piperazine-1-carbonyl)-4-fluorobenzyl)phthalazine-1(dihydro)-one according to claim 2 to the subject.

6. The method according to claim 5, wherein the subject has cancer.

7. The method according to claim 6, wherein the cancer comprises at least one of a gastric cancer, pancreatic cancer, leukemia, breast cancer, ovarian cancer, and prostate cancer.

* * * * *

UNITED STATES PATENT AND TRADEMARK OFFICE
CERTIFICATE OF CORRECTION

PATENT NO. : 10,874,667 B2  
APPLICATION NO. : 16/341255  
DATED : December 29, 2020  
INVENTOR(S) : Fan et al.

Page 1 of 1

It is certified that error appears in the above-identified patent and that said Letters Patent is hereby corrected as shown below:

On the Title Page

Item (73) Assignee:  
Delete:  
"Shanghai Huilin Life Scinece & Technology Co., Ltd., Shanghai (CN)"  
And Insert:  
-- Shanghai Huilun Life Science & Technology Co., Ltd., Shanghai (CN) --

Signed and Sealed this  
Eleventh Day of January, 2022

Drew Hirshfeld  
*Performing the Functions and Duties of the*  
*Under Secretary of Commerce for Intellectual Property and*  
*Director of the United States Patent and Trademark Office*